(12) United States Patent
Sica

(10) Patent No.: US 11,266,592 B2
(45) Date of Patent: *Mar. 8, 2022

(54) BODY BUTTER AND METHOD OF MANUFACTURE

(71) Applicant: Diane Sica, San Antonio, TX (US)

(72) Inventor: Diane Sica, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/197,694

(22) Filed: Nov. 21, 2018

(65) Prior Publication Data

US 2019/0231676 A1   Aug. 1, 2019

Related U.S. Application Data

(63) Continuation-in-part of application No. 15/882,897, filed on Jan. 29, 2018, now Pat. No. 10,137,076.

(51) Int. Cl.
*A61K 8/9789* (2017.01)
*A61K 8/92* (2006.01)
*A61Q 19/00* (2006.01)

(52) U.S. Cl.
CPC ............ *A61K 8/9789* (2017.08); *A61K 8/922* (2013.01); *A61Q 19/00* (2013.01)

(58) Field of Classification Search
None
See application file for complete search history.

(56) References Cited

U.S. PATENT DOCUMENTS 5,997,889 A * 12/1999 Durr ................ A61K 8/671
424/401
10,137,076 B1 * 11/2018 Sica ................ A61K 8/9789

* cited by examiner

*Primary Examiner* — Susan Hoffman
(74) *Attorney, Agent, or Firm* — Leavitt Eldredge Law Firm

(57) ABSTRACT

A body butter that includes a base oil, beeswax, shea butter, cocoa butter, and vitamin E oil.

13 Claims, 4 Drawing Sheets

BODY BUTTER AND METHOD OF MANUFACTURE

BACKGROUND

1. Field of the Invention

The present invention relates generally to massage oils.

2. Description of Related Art

Windshield rubber bumpers are well known in the art and are commonly used during massage sessions and other forms of relaxation and pain-relieving activities. One of the problems commonly associated with convention massage oils is the use of harmful substances added to the massage oils, which in turn are transferred within the body of the user. Great strides in the area of massage oils; however, many shortcomings remain. Accordingly, the present invention overcomes such problems commonly associated with conventional massage oils.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
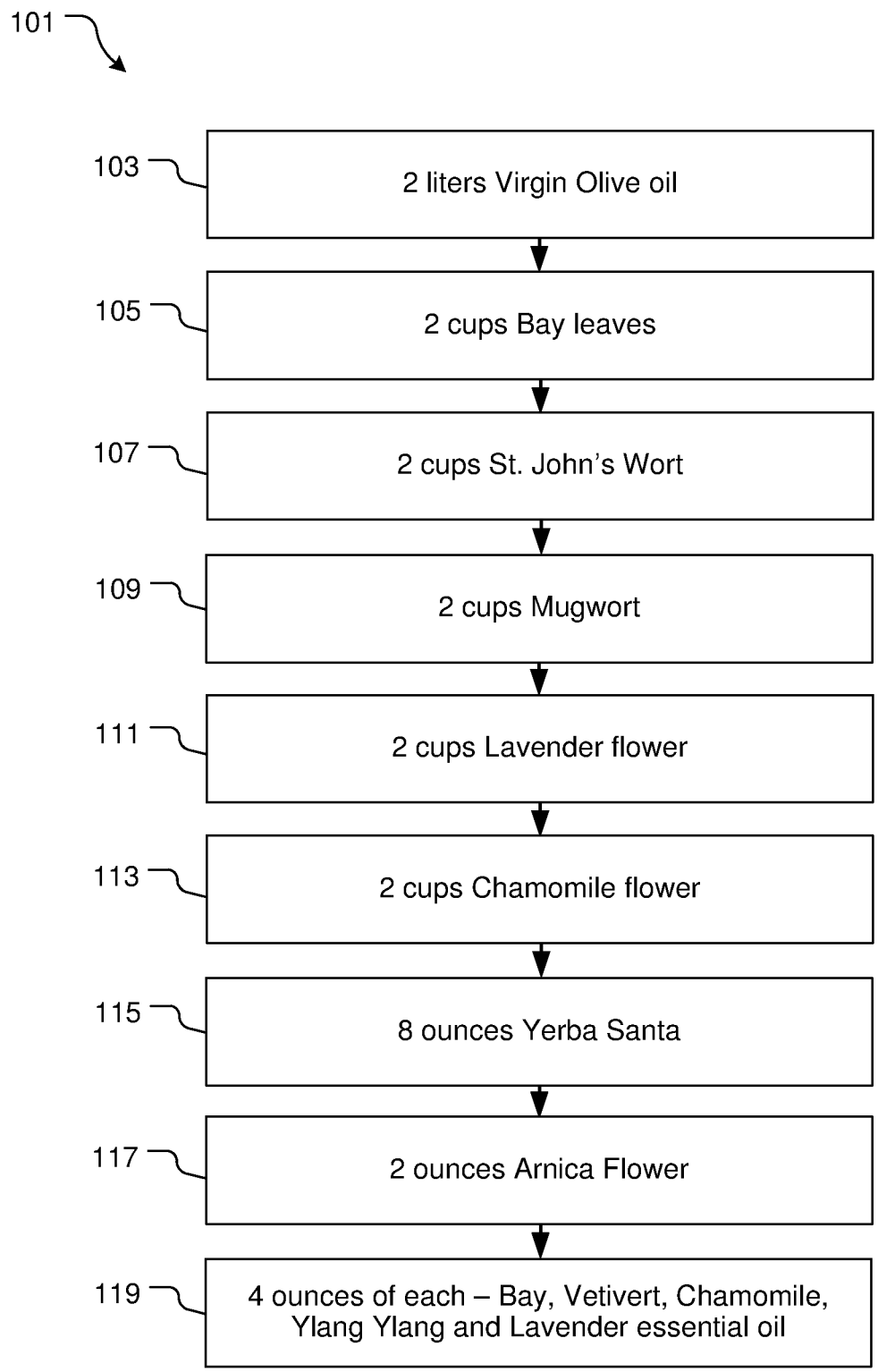
FIG. 1 is a flowchart of ingredients added to the message oil of the present invention.

While the recipe and method of manufacture of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the recipe and method of manufacture of the present application are provided below. It will of course be appreciated that in the development of any actual embodiment, numerous implementation-specific decisions will be made to achieve the developer's specific goals, such as compliance with recipe-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The recipe and method of manufacture will be understood, both as to its structure and operation, from the accompanying drawings, taken in conjunction with the accompanying description. Several embodiments of the recipe are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
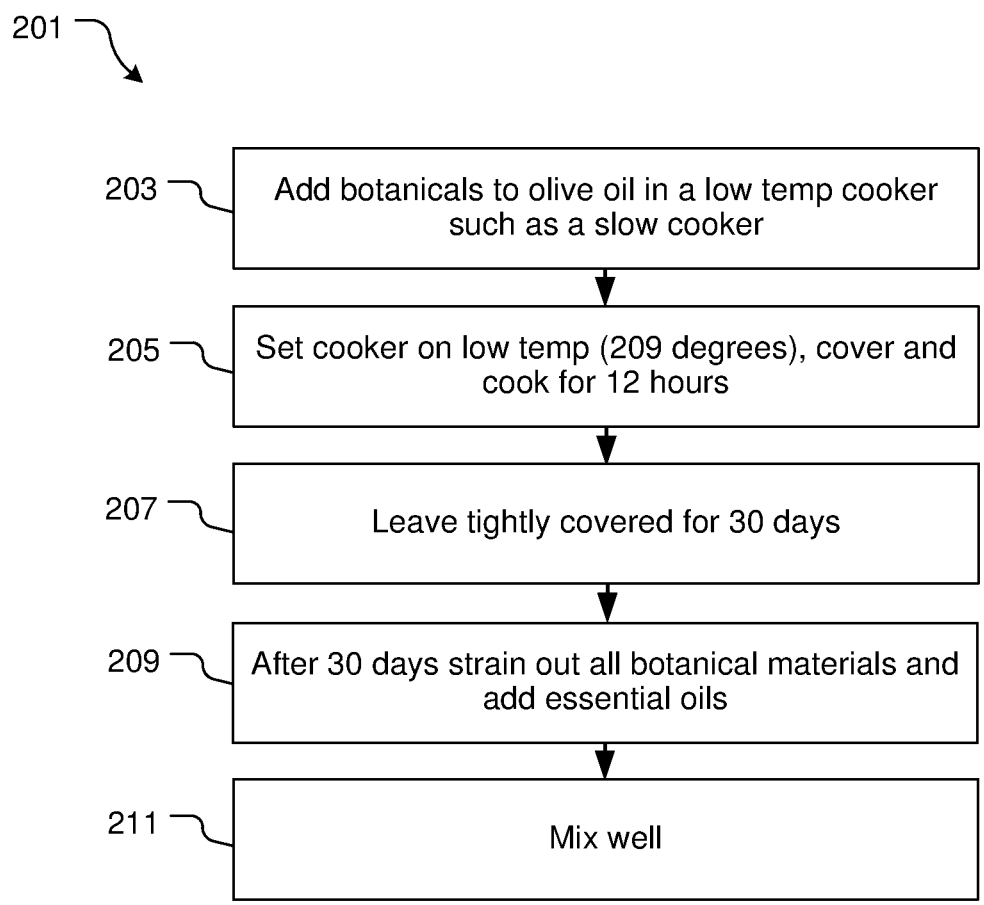
FIG. 2 is a flowchart of the preferred method of manufacturing the same.

Referring now to the drawings wherein like reference characters identify corresponding or similar elements throughout the several views, FIGS. 1 and 2 depict flow charts of a recipe and the manufacturing process of a message oil.

It will be appreciated that the present invention discloses an all-natural massage oil with analgesic benefits. An all-natural massage oil is disclosed, said oil formulated entirely from ingredients found in naturally-occurring plants (and excluding menthol), and having pain-relieving properties. Furthermore, said massage oil is non-toxic, and thus safe to use on children.

Some of the advantages of the present invention are: improved pain relief; improved massage experience; improved production costs due to use of economical plant matter; improved health for users; reduced toxicity to humans; and so forth.

Referring specifically to FIG. 1, a flowchart 101 of the preferred recipe to manufacture is shown. In the preferred embodiment, the ingredients include one or more of the following: 2 liters Virgin Olive oil; 2 cups Bay leaves; 2 cups St. John's Wort; 2 cups Mugwort; 2 cups Lavender flower; 2 cups Chamomile flower; 8 ounces Yerba Santa; 2 ounces *Arnica* Flower; 4 ounces of each—Bay, Vetivert, Chamomile, Ylang Ylang and Lavender essential oils. These features are shown in boxes 103-119 of the flowchart.

It should be understood that the exemplary embodiment of the recipe includes the described ingredients in the defined quantity. However, alternative embodiments could include more or less of these ingredients in the same or different quantities; all falling within the scope of the present invention.

In FIG. 2, a flowchart 201 depicts the preferred method of manufacturing, which includes adding the abovementioned botanicals ingredients to olive oil in a low temp cooker such as a slow cooker. Set cooker on low temp (209 degrees), cover and cook for 12 hours. Leave tightly covered for 30 days. After 30 days strain out all botanical materials and add essential oils. Mix well. These features are shown in boxes 203-211 of the flowchart.

It should be understood that the exemplary embodiment of the method of manufacturing includes the described steps along with defined temperatures and duration of time. However, alternative embodiments could include more or less of these steps and alterations of time for each step in the manufacturing process.

Figure 3:
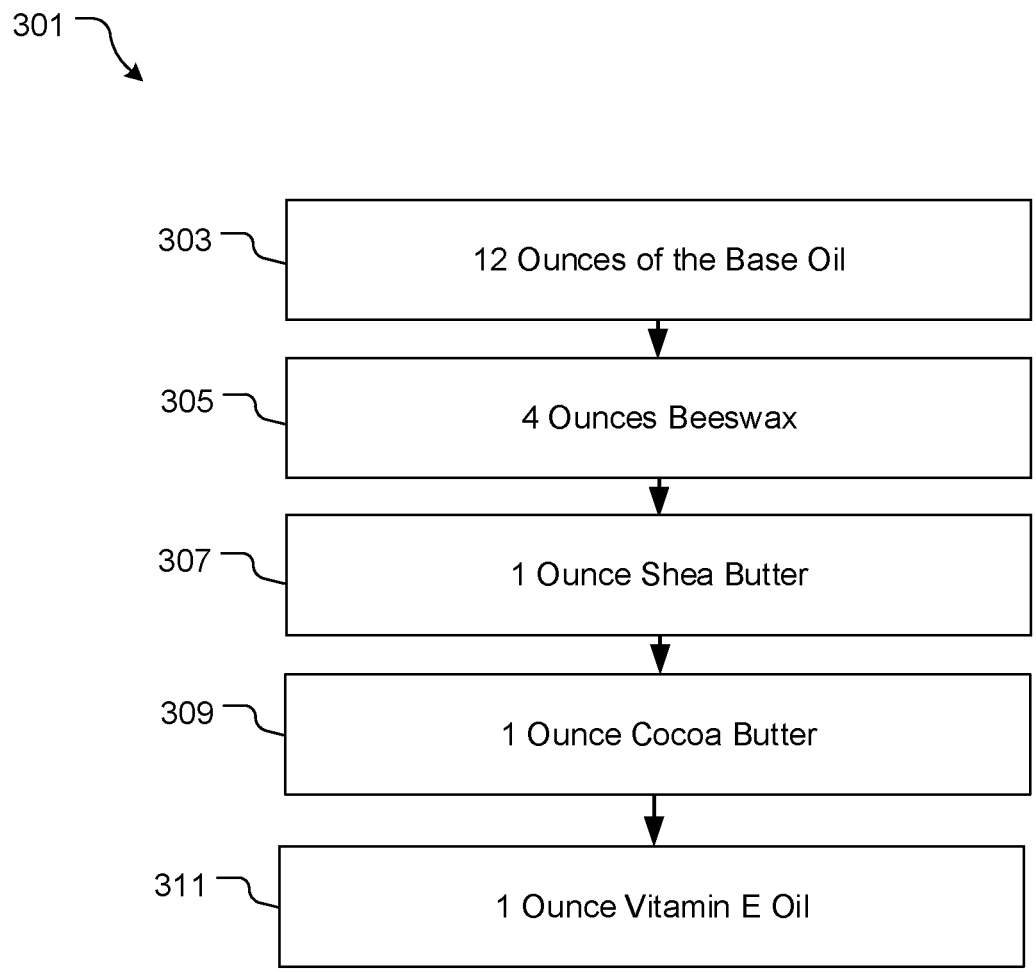
FIG. 3 is a flowchart of ingredients utilizing the oil of FIG. 1 to create a body butter.
Figure 4:
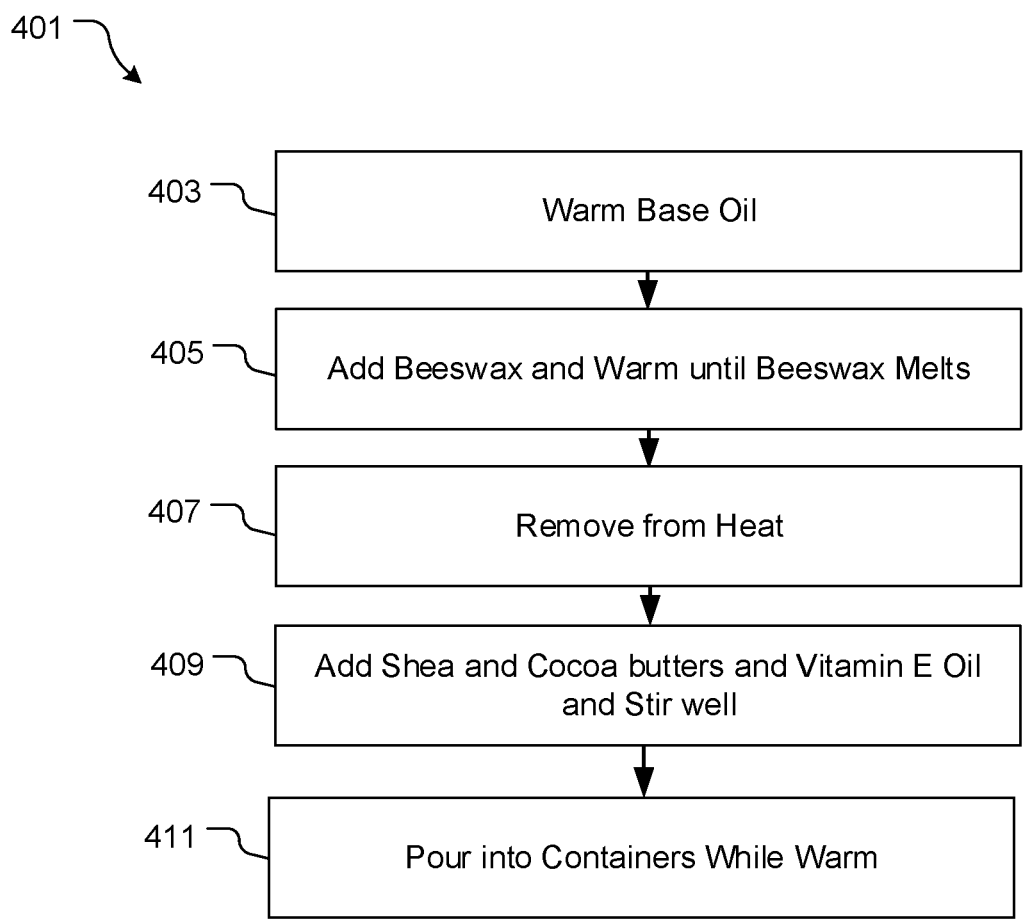
FIG. 4 is a flowchart of the preferred method of manufacture of the body butter.

In FIGS. 3 and 4, flowcharts 301 and 401 depict the preferred recipe and manufacture process contemplated for the creation of a body butter, wherein the oil described above is utilized as a base oil. The message oil includes one or more of the following: 12 ounces of the base oil; 4 ounces of beeswax; 1 ounce of shea butter; one ounce of cocoa butter; and one ounce of vitamin E oil, as shown with boxes 303, 305, 307, 309, 311.

In FIG. 4, a flowchart 401 depicts the preferred method of manufacture, which includes warming the base oil, adding in the beeswax and warm until the beeswax melts, as shown with boxes 403, 405. Then the base oil and beeswax is removed from heat, and the shea and cocoa butters, and vitamin E oil are added and the stirred in well, as shown with boxes 407, 409. The mixture is then poured into one or more containers while still warm, as shown with box 411.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A body butter comprising:
    a base oil including:
        Virgin Olive oil;
        Bay leaves;
        St. John's Wort;
        Mugwort;
        Lavender flower;
        Chamomile flower;
        Yerba Santa;
        Arnica Flower;
    4 ounces of each of the following:
        Bay essential oil;
        Vetivert essential oil;
        Chamomile essential oil;
        Ylang Ylang essential oil; and
        Lavender essential oil;
    beeswax;
    shea butter;
    cocoa butter; and
    vitamin E oil.
2. The body butter of claim 1, wherein the Virgin Olive oil is 2 liters.
3. The body butter of claim 1, wherein the Bay leaves is 2 cups.
4. The body butter of claim 1, wherein the St. John's Wort is 2 cups.
5. The body butter of claim 1, wherein the Mugwort is 2 cups.
6. The body butter of claim 1, wherein the Lavender flower is 2 cups.
7. The body butter of claim 1, wherein the Chamomile flower is 2 cups.
8. The body butter of claim 1, wherein the Yerba Santa is 8 ounces.
9. The body butter of claim 1, wherein the *Arnica* Flower is 2 ounces.
10. The body butter of claim 1, wherein the beeswax is 4 ounces.
11. The body butter of claim 1, wherein the shea butter is 1 ounce.
12. The body butter of claim 1, wherein the cocoa butter is 1 ounce.
13. The body butter of claim 1, wherein the Vitamin E oil is 1 ounce.

* * * * *